United States Patent
Vercauteren et al.

(10) Patent No.: US 12,303,758 B2
(45) Date of Patent: May 20, 2025

(54) SPORTS TRAINING SYSTEM AND METHOD

(71) Applicant: LEDSREACT, Harelbeke (BE)

(72) Inventors: Koen Vercauteren, Wevelgem (BE); Lander Vandecaveye, Desselgem (BE); Eli Clement, Wondelgem (BE); Matthew Philpott, Wetteren (BE); Pieter Lesage, Wijnegem (BE); Alexander Crolla, Berchem (BE)

(73) Assignee: LEDSREACT, Harelbeke (BE)

( * ) Notice: Subject to any disclaimer, the term of this patent is extended or adjusted under 35 U.S.C. 154(b) by 91 days.

(21) Appl. No.: 18/018,465

(22) PCT Filed: Jul. 28, 2021

(86) PCT No.: PCT/EP2021/071211
§ 371 (c)(1),
(2) Date: Jan. 27, 2023

(87) PCT Pub. No.: WO2022/023446
PCT Pub. Date: Feb. 3, 2022

(65) Prior Publication Data
US 2024/0009537 A1    Jan. 11, 2024

(30) Foreign Application Priority Data

Jul. 31, 2020   (EP) .................................... 20188871

(51) Int. Cl.
*A63B 69/00* (2006.01)
*A63B 24/00* (2006.01)
(52) U.S. Cl.
CPC ...... *A63B 69/0053* (2013.01); *A63B 24/0021* (2013.01); *A63B 2024/0025* (2013.01);
(Continued)

(58) Field of Classification Search
CPC ............ A63B 69/0053; A63B 24/0021; A63B 2024/0025; A63B 2220/10;
(Continued)

(56) References Cited

U.S. PATENT DOCUMENTS

| 11,238,398 B2* | 2/2022 | Lau ......................... H04W 4/02 |
| 2003/0077556 A1* | 4/2003 | French .................. A61B 5/1118 |
| | | 434/258 |

(Continued)

FOREIGN PATENT DOCUMENTS

EP    3181202 A1    6/2017

OTHER PUBLICATIONS

International Search Report from PCT Application No. PCT/EP2021/071211, Oct. 19, 2021.
(Continued)

*Primary Examiner* — Megan Anderson
*Assistant Examiner* — Andrew M Kobylarz
(74) *Attorney, Agent, or Firm* — Workman Nydegger

(57) ABSTRACT

A sports training system for exercising reaction to stimuli, includes at least one stimulus generator being configured to generate a stimulus indicative for a physical movement to be performed by a user; at least one sensor configured to measure a position of the user at predetermined time intervals during performance of the physical movement; a controller configured to control the at least one stimulus generator.

13 Claims, 2 Drawing Sheets

(52) U.S. Cl.
    CPC ....... *A63B 2220/10* (2013.01); *A63B 2220/30* (2013.01); *A63B 2220/89* (2013.01)

(58) Field of Classification Search
    CPC ............ A63B 2220/30; A63B 2220/89; A63B 2024/0068; A63B 2071/0675; A63B 2225/74; A63B 71/0622; A61B 5/0004; A61B 5/1126; A61B 5/162; A61B 5/112
    See application file for complete search history.

(56) References Cited

U.S. PATENT DOCUMENTS

2015/0081057 A1\* 3/2015 Hamada ........... A63B 21/00181
                                                    700/91
2019/0038932 A1\* 2/2019 Eckblad .................... G06F 8/40

OTHER PUBLICATIONS

Search Report from corresponding European Application No. 20188871.6, Jan. 26, 2021.

\* cited by examiner

SPORTS TRAINING SYSTEM AND METHOD

FIELD OF THE INVENTION

The present invention generally relates to sports training systems and in particular to developing and training reaction skills to stimuli.

BACKGROUND OF THE INVENTION

Sports training devices and systems are generally known and are widely used in various sports disciplines, for example in football, tennis, basketball, or other sports. These sports training systems can include training reaction skills to stimuli, in order to minimize the time between the generation of the stimuli and the reaction of the users, which is not only a physical but also a mental training. Training one's reaction time is useful for example in football, in basketball, in athletics, in swimming, in volleyball, in handball, in tennis, in baseball, in cricket, in American football, and in any other sport where running trajectories or reactions must be adapted in function of stimuli, such as the sound of a starting pistol in athletics and in swimming, or the shot of a penalty in football, or passes, or of a drop shot in tennis.

An example of a such a training device for exercising reaction to stimuli has been disclosed in EP3181202A1. The device includes two or more stimuli, for example visual signals, which are indicative of a direction of movement. The device further includes a proximity sensor. When the proximity sensor senses the presence of a user, a stimulus is generated, i.e. a LED lamp lights up, triggering the user to move along the direction indicated by the stimulus. In this way, the user can train his reaction speed and speed of change of direction, which are useful skills in a large number of sports. Even if the device can discriminate between good and bad reaction to stimuli and can log reaction times over time to evaluate progress, the device is unable to tell the user in more detail in which part of an exercise progress can be made. A reaction time to a stimulus may be good, but acceleration may for example still be slow. The user may move in the right direction as indicated by the stimulus but may for example not take the shortest route.

It is also known to visually track the performance of a user, for example by using a camera and recording the performance of a user during training allowing the trainer and/or user to watch and visually analyse the recording of the physical movements during the performance. However, such a visual analysis is time intensive and providing immediate feedback to the user is expensive in terms of processing power and storage capacity. Moreover, such visual recordings can for example not give detailed information on reaction time or speed of movement. Additionally, there may be privacy issues involved. On top of that, visual recordings are relatively sensitive to light conditions and quality can quickly deteriorate both at night-time, during rainfall or when there is too much direct sunlight.

Still other sports training systems use identification technology, such as for example RFID or Bluetooth or other, to track a user during performance of a movement. These technologies require however a wearable element to be worn by the user during training, which may hinder a user's movements and impair his or her performances. Moreover, battery capacity of each wearable element and of a central unit need to be managed.

US 2003/0077556 discloses an education system for engaging a student in a kinaesthetic learning process. The system uses a wireless optical position tracker for continuously tracking and determining a student's position during movement in a defined physical space. Since the student needs to wear a passive or active reflector or beacon, the student's movements may be hampered by the reflector or beacon. Moreover, the system is imposing the exercises rather than reacting to a student's movement. Finally, it may be cumbersome to use the system outside since it is based on virtual reality needing a large video screen.

It is therefore an aim of the present invention to solve or at least alleviate one or more of the above-mentioned problems. In particular, the invention aims at providing a sports training system and a sports training method allowing a relatively complete assessment of the performance of a user without hindering a user's performance.

SUMMARY OF THE INVENTION

To this aim, according to first aspect of the invention, there is provided a sports training system. In particular, the sports training system for exercising reaction to stimuli comprises at least one stimulus generator being configured to generate a stimulus indicative for a physical movement to be performed by a user, at least one sensor configured to measure a position of the user at predetermined time intervals during performance of the physical movement, and a controller configured to control the at least one stimulus generator. In an inventive way, the controller is also configured to derive a trajectory of the user during performance of the physical movement from the position measurements by the at least one sensor. In the context of the present application, a trajectory is to be understood as defined in a dictionary, i.e. a trajectory of a moving object is the path that the object follows as it moves. A trajectory or a path is therefore more than just a distance to a sensor which is one-dimensional, whereas a trajectory is two or three dimensional. The system may comprise a single sports training device, for example a main training device, including the at least one stimulus generator, the at least one sensor and the controller. Alternatively, a main training device may for example include the at least one sensor and the controller while the at least one stimulus generator may be a separate device controllable by the controller. The at least one stimulus generator, the at least one sensor and the controller may also be separate devices. Deriving the trajectory of the user can provide valuable information on the performance of a physical movement triggered by the generated stimulus, which goes beyond reaction time or the time needed to perform the movement. As an example, a stimulus can be generated which is indicative of moving towards a predetermined checkpoint and back while watching a same direction. By measuring a position of the user at predetermined time intervals during performance of said physical movement and by deriving the trajectory of the user during performance of the physical movement, the user can know for example that the movement in a first part was relatively quick or slow but better or worse at a further part of the physical movement. If only reaction time were measured between generation of the stimulus and performance of the desired movement, or even if time for performing the physical movement was measured, this additional information would not be available and the user would not know how to improve its performance of the physical movement.

The physical movement which is to be performed by the user and which is triggered by the stimulus generated by the at least one stimulus generator can for example include moving, for example running forward or backward, walking, jumping, swimming, or any other kind of moving, in an indicated direction, for example straight in front, back, to the left or to the right. The physical movement may for example comprise a go-and-back movement towards and back from a predetermined checkpoint. The physical movement may for example also include jumping at a predetermined height.

The stimulus generator may for example be configured to generate a visual stimulus, such as a light signal. The visual stimulus may for example include a continuous signal or a flashing or a blinking signal. The visual stimulus may include different colours, such as red, blue, green, etcetera. The stimulus generator may for example include a LED light, or an RGB LED light, or any other type of suitable lighting. The stimulus may be indicative for a direction of movement, for a way of moving, for a number of times a movement is to be performed or for any other aspect of a physical movement. By combining a light signal with a colour and/or a way of signalling, a large variety of stimuli may be generated by a single stimulus generator. In case of a plurality of stimulus generators, a position of the stimulus generator on the training device may be indicative for a direction of movement. The sports training system may for example include a stimulus generator at one or more edges of the device, each edge being directed into a different direction. Alternatively, the system may include a stimulus generator configured to generate an auditive signal, or any combination of a visual and/or an auditive signal.

The controller is preferably also configured to measure and/or derive a speed, a direction of movement and/or an acceleration of the user during performance of the physical movement from the measurements by the at least one sensor. Depending on a type of sensor, speed and/or a direction of movement may be measured directly by the at least one sensor or may be derived from the data, i.e. position measurements, measured by the at least one sensor. Knowing the position of the user over time during performance of the physical movement can allow deriving a speed and/or acceleration of the user over time, which can give additional information to the user on the performance of the physical movement. Speed and/or acceleration can for example be better or worse at one moment of the performance than at another moment. Having this information can allow an amendment of a training program to improve certain aspects of the physical movement.

The controller may advantageously be configured to control the at least one stimulus generator based on the measurements by the at least one sensor or based on data derived from the measurements by the at least one sensor. The controller may for example transmit a signal to the at least one stimulus generator once a user has been detected through position measurement by the at least one sensor at a predetermined position, which may be called a checkpoint, within a range of detection of the at least one sensor. Having received said signal from the controller, the stimulus generator can then generate a stimulus to the user. Such a signal may be transmitted to the stimulus generator at a beginning of a training session to initiate a training session or during training, so that the user can determine a training pace rather than the training system imposing a training pace to the user. The controller can be configured to include a plurality of said predetermined checkpoints, which may be predetermined areas or predetermined lines. The controller may be configured to transmit a signal to the at least one stimulus generator when the at least one sensor measures a presence of the user within such a predetermined surface or a crossing of such a predetermined line by the user. Instead of immediate feedback from the controller to the at least one stimulus generator, the controller may also be configured to control the stimulus generator based on the data on the performance of the physical movement derived from the measurements by the at least one sensor, for example based on a derived speed and/or acceleration. The controlling of the stimulus generator may include an immediate transmission of a control signal to the stimulus generator or may include amendments of a training exercise including a succession of stimuli at a later stage. In this way, a predetermined scheme of stimuli forming a training exercise may be amended in function of the derived performance data of the physical movement, adding for example additional repetition of movements which were not performed well enough, immediately or at a next use of the system by the user. Alternatively, the sports training system may include a start button, and/or may include a predetermined set of exercises including one or more generations of stimuli, from which the user can choose one to be executed via an interface of the sports training system.

The sports training system may further comprise at least one beacon configured to indicate a predetermined distance from the at least one sensor. The at least one beacon can allow to visualize predetermined positions to be reached by the user during a physical movement, such as for example the so-called checkpoints. As an example, a stimulus may be generated to move, for example run, to a predetermined location at a predetermined distance from the at least one sensor. This location may be indicated by a physical beacon so that a user can see which position he needs to go to or to cross. The at least one beacon is preferably detectable by the at least one sensor. In case of a radar sensor, the beacon may for example include a movable reflective element. The controller may for example be configured to transmit a signal during placement of the at least one beacon once the at least one sensor detects correct positioning of the at least one beacon according to a predetermined set of checkpoints. The beacons may also be entirely virtual and may correspond to a predetermined and/or pre-programmed checkpoint of which a position with respect to the at least one sensor is known to the controller.

The at least one beacon may also include a stimulus generator which is controllable by the controller. The stimulus generator included in the at least one beacon may be an additional stimulus generator, next to at least another stimulus generator, for example on a main training device including the at least one sensor and/or the controller. Or the at least one stimulus generator of the training system may be included only on the at least one beacons or may be separate from the at least one beacon and from the main training device. In this way, stimuli may be generated on the beacon, which may be visible more easily when the user may be at a relatively large distance from the at least one sensor or from the main training device. It can also allow a relatively large variety of stimuli to be generated.

The at least one sensor can preferably be configured to non-visually measure the position of the user during performance of the physical movement. The at least one sensor can for example include at least one radar or lidar. As is known to the person skilled in the art, a radar is configured to emit a beam of radio waves and to receive a reflection of said beam, which can provide information on the position and/or speed of the object that reflected the beam of radio waves. A lidar has a similar way of functioning but is configured to use infrared laser waves rather than radio waves. By using a radar to measure a position of a user over time during performance of the physical movement triggered by the generated stimulus, a trajectory of the user can be derived in a relatively quick and reliable way without hindering the user in performing the physical movement since the user does not need to have any wearable item to allow his position to be measured by the radar. Moreover, radar technology allows a relatively large range of measurement, which may be beneficial in some sports training, such as for example in football. Since no visual information is collected with respect to the user, there are no privacy issues either. Alternatively, the at least one sensor may also include a camera configured to visually measure the position of the user during performance of the physical movement.

The at least one sensor may for example be configured to measure a position of the user at a rate of at least 20 Hertz. This rate of measurement can already allow relatively precise position measurements of the user during performance of a physical movement to allow a trajectory to be derived from the position measurements. The rate can also allow to derive speed and/or acceleration at a reasonable precision or accuracy. A higher rate of measurement can allow higher accuracy, but will require more processing power of the controller, and will therefore be more expensive.

A measurement range of the at least one sensor is adjustable. A measurement range is to be understood as a range of distance from the at least one sensor in which the at least one sensor can provide position measurements of the user at a predetermined level of accuracy. The measurement range can for example include a range between 1 cm and 150 m from the sports training system, in particular from the main training device, preferably between 1 cm and 50 m from the sports training device, more preferably between 10 cm and 30 m. In case of a radar, the power of the emitted beam of radio waves can be adjustable to adjust the measurement range and/or accuracy of measurements. The beam being emitted as a cone or an elliptical cone, a solid angle of said cone of the emitted radio waves may also be adjustable between for example a relatively wide solid angle with a relatively small measurement range and a relatively small solid angle and a relatively large measurement range depending on the desired kind of training exercise.

The sports training system can advantageously comprise at least two sensors, each being configured to measure the position of the user within a respective detection beam at predetermined time intervals during performance of the physical movement. The at least two sensors may for example be positioned such that the respective detection beams are directed into opposite or complementary directions. The sports training system may for example include two sensors having a detection beam covering more or less 180°, which are each directed into opposite directions such that the two sensors can together more or less cover 360°. Alternatively, three sensors having a detection beam covering more or less 120°, or four sensors having a detection beam covering more or less 90° may be positioned such that they can together more or less cover 360°. At least two sensors may also be positioned at different angles in a plane transverse to a plane on which the sports training system is placed. In said transverse plane, the respective detection beams can also be adjusted to be complementary to each other. Multiple sensors may thus be used to improve accuracy over a relatively wide angle. Additionally, and/or alternatively, the at least two sensors may each be configured to measure the position of a different user, such that the system can be used for a simultaneous training of a plurality of users corresponding to the number of sensors. Each user may then receive stimuli in function of its own performance as detected by its respective sensor.

It may be preferred that a first detection beam of one of the at least two sensors at least partly overlaps with a second detection beam of another of the at least two sensors. In the overlap of the first and the second detection beam, position measurements of the at least two sensors can be combined, and the derived data can achieve a higher accuracy than with a single detection beam. Additionally, combination of data in the overlapping zone of the first and the second detection beam may compensate a reduced accuracy in position measurement at outer regions of a first or second detection beam, which may provide position measurements with a higher accuracy in a central area than in outer areas of the detection beams. The sports training system may therefore for example include four sensors which are placed towards different directions in angles of more or less 90° with respect to each other while each of them having a detection beam covering more or less 120°. As such, each of the four sensors can cover an area of more or less a quadrant with overlapping detection beams in the outer areas where accuracy of the position measurements by the sensor would decrease without overlapping detection beams of two sensors. In case of at least two sensors placed at different angles in a plane transverse to a plane on which the sports training system is placed, one sensor can for example be placed under an angle of more or less 5° with respect to the plane of placement of the training system, which can be beneficial to reduce noise in the data due to moving grass if the training system is placed on the ground, for example on a lawn. A second sensor may for example be placed at a higher angle with respect to the ground, for example at an angle of more or less 20°. The first and the second sensor may then have respective detection beams which have a relatively large overlap allowing for example to derive a height of a jump of a user.

The controller may advantageously be configured to derive a trajectory of an object during performance of the physical movement from the position measurements by the at least one sensor. Such an object may for example be a ball, such as a basketball, a football, or a tennis ball, or may be a tennis racket or a hockey stick, or any other object involved in sports training. The sensor and/or controller can for example include a filtering procedure configured to distinguish between a physical movement of a user and a moving object in the same field of measurement. As a result, position measurements can not only be obtained for the user but also for an object in relation with the user, for example a sports attribute such as a ball or racket, and a trajectory of the object can be derived, which can again allow a more complete assessment of a physical movement of a user, such as for example a combination of the user moving and hitting a ball.

The sports training system can comprise an interface configured to display data derived by the controller related to the performance of the physical movement. The interface may comprise a display, such as screen, for example to graphically display a trajectory derived by the controller from the position measurements by the at least one sensor. In this way, the user can receive feedback relatively quickly after having performed the physical movement triggered by the at least one stimulus generator. Other derived data, such as for example speed and/or acceleration, on the performance of the physical movement may also be displayed on the interface. The interface may also be configured to allow controlling the at least one stimulus generator, for example by allowing making a choice between predetermined exercises each including one or more stimuli, for example a succession of predetermined stimuli. The interface may also be configured to allow a direct controlling of the stimulus generator or a control of the staring of the stimulus generator.

The sports training system can preferably comprise a communication unit configured to transmit data related to the performance of the physical movement to a central computing unit for further analysis and/or storage of the data. The communication unit can for example transmit the position measurements and the derived speed related to the performance of a physical movement to a central, for example remote, computing unit, and the central computing unit may for example derive acceleration over time from the data transmitted by the communication unit. In this way, some of the processing can be done remotely, which can save processing power on the sports training system itself. The central computing unit may for example be a dedicated server including dedicated processors, or a cloud-based computing unit. The communication unit may be comprised in a main training device of the system or may be a separate and/or remote unit.

It is still more preferred that the communication unit is configured to receive instructions for the at least one stimulus generator from the central computer unit and/or from a mobile communication device, so as to allow remote interaction with the sports training system. The sports training system may for example be activated through an application on a mobile communication device. The mobile communication device may for example also allow a choice of an exercise among a predetermined set of exercises of a physical movement including at least one stimulus to be generated. The mobile communication device may for example include all functions of the interface, for example also displaying feedback on the performance of the physical movement. The communication unit can for example also receive instructions from the central computing unit, for example based on the position measurements by the at least one sensor and the data derived therefrom by the controller and/or the central computing unit. In this way, the controller can for example amend a predetermined scheme of stimuli in function of the performance of the triggered physical movement and target training on weaknesses in the performance of the physical movement, which may be done immediately, during a next exercise or during a next use of the training system by the user. The communication unit may allow connection, for example via Bluetooth or any other known technology, to other devices configured to provide information on a user of the training system. As an example, a user of the training system may be provided with a heart rate sensor, for example via a mobile application. The communication unit may be configured to receive information from an external application on for example a user's heart rate, which may be transmitted to the controller. The controller may then for example amend a rate of succession of stimuli to the user in function of the measured and transmitted heart rate.

The sports training system can advantageously comprise a central computing unit configured to analyse the data received from the communication unit. The analysis may include deriving acceleration over time from the data, such as position and/or speed measurements, transmitted by the communication unit. The analysis may also comprise comparison of data relating to a predetermined scheme of stimuli over time. A given physical movement triggered by one or more stimuli may for example be repeated several times as a training by the same user. The central computing unit may then be configured to analyse evolution of predetermined parameters over time, for example compare speed, acceleration, or any other derived information in a first, second or next performance of the physical movement. In this way, the user and/or the trainer can obtain valuable information for the assessment of the performance of a physical movement on a long-term basis. As such, the sports training system may be used both for evaluation of performance as for training. Based on acquired training data, the central computing unit can also provide a user with recommended training exercises.

According to a second aspect of the invention, there is provided a sports training method for exercising reaction to stimuli. Such a sports training method can provide one or more of the above-mentioned advantages.

DETAILED DESCRIPTION OF EMBODIMENT(S)

Figure 1:
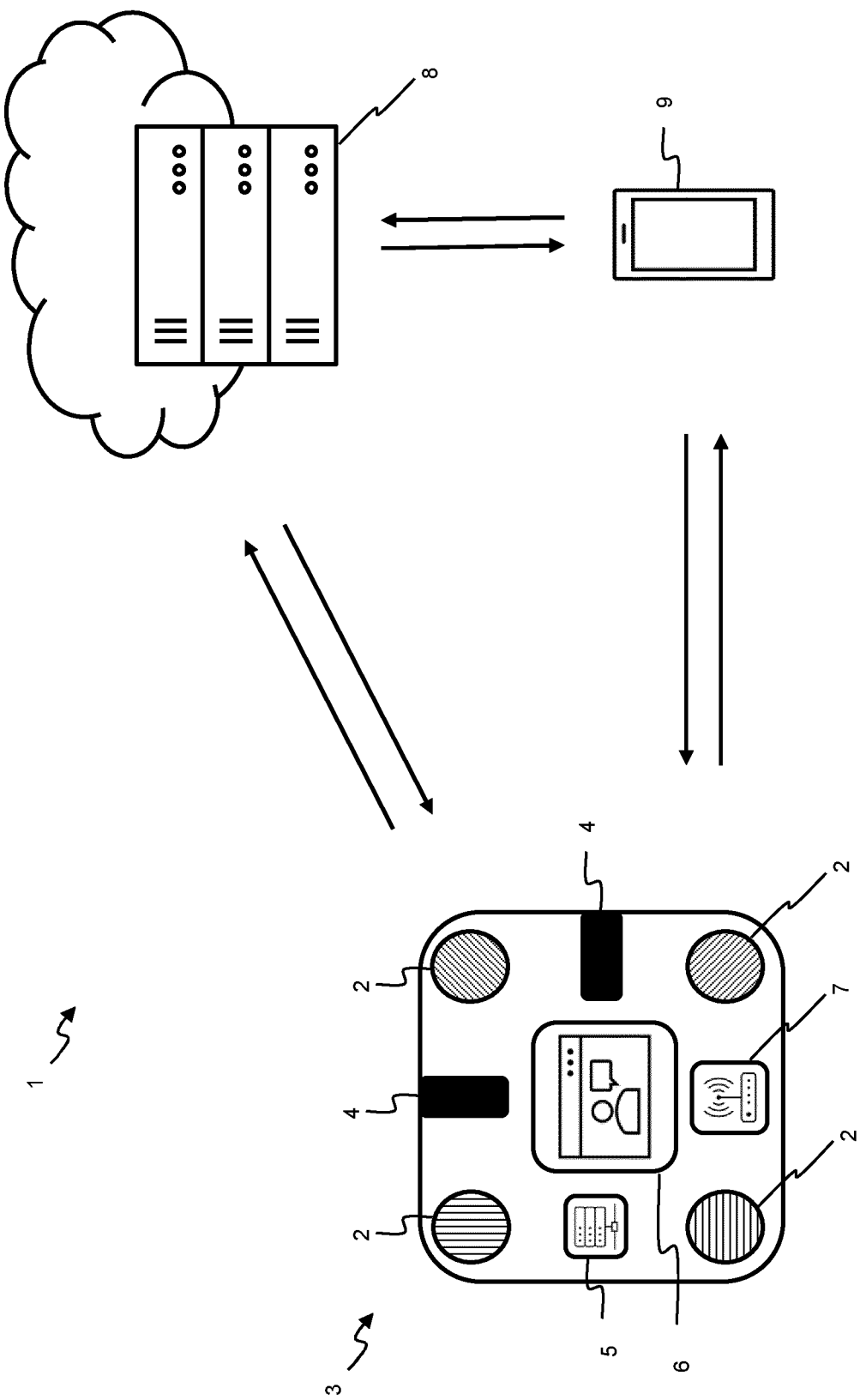
FIG. 1 shows a schematic view of a preferred embodiment of sports training system according to the present invention.

FIG. 1 shows a schematic view of a preferred embodiment of sports training system according to the present invention. The sports training system 1 comprises at least one stimulus generator 2, for example four stimulus generators 2 being configured to generate a stimulus indicative for a physical movement to be performed by a user. These stimulus generators 2 can for example be four RGB-LEDs, for example each LED having a different colour. These four stimulus generators 2 may for example be mounted on a main training device 3 but can also be separate devices. The main training device 3 may for example have a substantially round or substantially square shape or any other shape, for example having a diameter in a range of more or less 15 cm to more or less 50 cm, preferably around 30 cm. It may have a plastic cover allowing to be used in rainy conditions. The system 1 further comprises at least one sensor 4, for example two sensors, configured to measure a position of the user at predetermined time intervals during performance of the physical movement. These two sensors can preferably be radar sensors which are configured to non-visually measure a position, speed and/or direction of movement of a user. The sensors can be placed on the main training device 3. They can be placed such that their respective detection beam is pointed in a different direction. The respective detection beams may for example have an angle of more or less 120°, or more or less. In case of a placement in an angle of more or less 90° between each other as illustrated, the respective detection beams of the sensors may have a partial overlap such that a user within said overlap can be detected by both radar sensors. The system 1 may also have a single sensor, or for example four sensors, or more. The sensors can be placed such that all sensors together can cover a range of 360°, or less. Two sensors 4 may also be placed one above the other, for example a first sensor at an angle of more or less 5° with respect to the plane of placement of the main training device 3, and a second sensor 4 at an angle of more or less 30° with respect to said plane of placement, which may be advantageous for measuring performance related for example to jumping. The sports training system 1 further comprises a controller 5 configured to control the at least one stimulus generator 2. The controller 5 may for example transmit a starting instruction to the at least one sensor stimulus generator 2. The controller is also configured to derive a trajectory of the user during performance of the physical movement from the position measurements by the at least one sensor 2. The controller 5 can for example be mounted on the main training device 3 or can be arranged as a separate device. In this preferred embodiment, the system 1 can further comprise an interface 6, for example also mounted on the main training device 3. The interface 6 can be configured to display data derived by the controller 5 related to the performance of the physical movement, such as for example the trajectory and/or speed of the user during performance of the physical movement. The interface 6 can for example include a screen, a touch screen and/or one or more buttons. The buttons can allow a user to select a training exercise from a set of training exercises, each training exercise including a predefined set of stimuli, as will be explained in more detail with FIG. 2. The screen can allow displaying, for example graphically or otherwise, the trajectory of the user during performance of a physical movement, or data derived therefrom, such as speed or acceleration. The sports training system can further comprise a communication unit 7 configured to transmit data related to the performance of the physical movement to a central computing unit 8 for further analysis and/or storage of the data. The communication unit 7 may for example be integrated into the main training device 3. In order to allow a smaller processor for the controller 5, the communication unit 7 can transmit data measured by the sensors 4, such as position and/or speed and/or reaction time of the user, and derived data, such as a trajectory of the user over time, to an external computing unit 8, which can do more intensive processing, for example deriving acceleration during performance of the physical movement. The computing unit 8 can for example be a dedicated server or a cloud-based processing unit. The computing unit 8 can also be configured to store and/or analyse data related to the performance of a physical movement by the user so that an analysis and comparison can be made between different performances of a same physical movement over time. In this way, evolution of the performance of a given physical movement, in a testing or training situation, can be evaluated efficiently. The communication unit 7 can further be configured to receive instructions for the at least one stimulus generator 2 from the central computing unit 8. Based on a further analysis of the data related to the performance of a physical movement, which may have been transmitted to the central computing unit 8 more or less in real time, or which may have been stored on the central computing unit 8 from previous performances, the central computing unit 8 may be configured to transmit instructions via the communication unit 7 and the controller 5 to the at least one stimulus generator 2. For example, if an analysis of the data shows a better performance of the user when the physical movement goes to the right than to the left, then the instructions to the stimulus generator 2 may be such as to generate a larger number of stimuli for a movement to the left than to the right to train the user in aspects of the physical movement in which the user seems to perform less well. The communication unit may also be configured to receive instructions for the at least one stimulus generator 2 from a mobile communication device 9. The sports training system 1 may include an application for a mobile communication device 9 configured to receive and display data related to the performance of the physical movement transmitted to the mobile communication device 9 by the central computing unit 8 or by the controller 5 via the communication unit 7. After studying these data, a user may send instructions via the communication unit 7 and the controller 5 to the at least one stimulus generator 2 to amend a predefined set of stimuli of a training exercise. The application can for example also allow programming of a sequence of stimuli to be generated by the at least one stimulus generator 2, or allow selection of a training exercise, as can be done from the interface 6 on the main training device 3. The interface 6 and the application on a mobile communication device 9 may have substantially the same functionalities, or they may have complementary functionalities. However, the application on a mobile device is optional since control of the system 1 can also be done via the interface 6 on the main training device 3 only. In case of a system without interface 6 on the main device 3, the mobile communication device can take the place of the interface 6. The mobile communication device 9 may also be configured to transmit additional information on the user to the controller 5 via the communication unit 7, for example information on a heartbeat rate of the user during performance of the physical movement. In this way, the controller 5 may amend a rate of succession of stimuli in function of a user's heartbeat.

Figure 2:
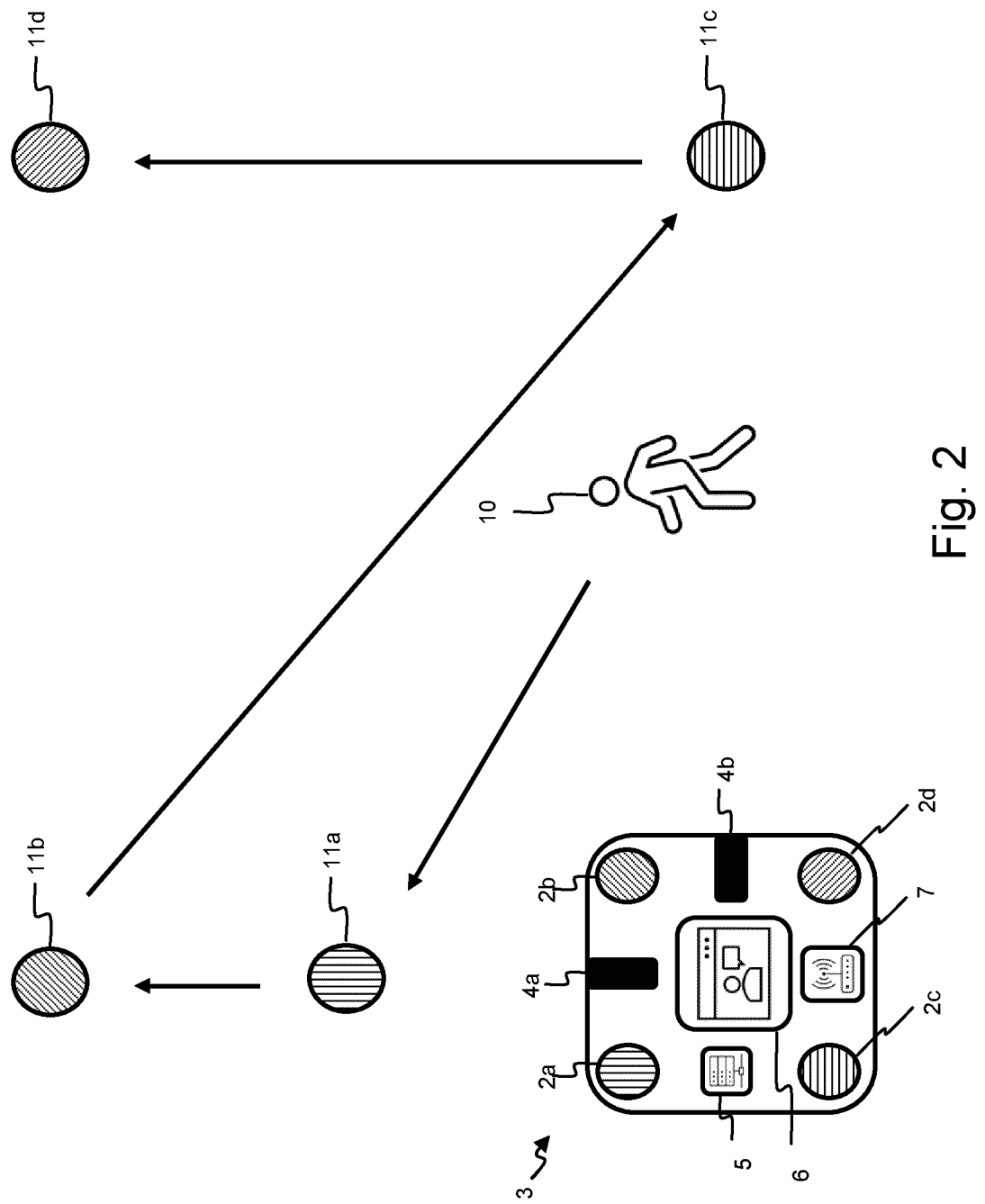
FIG. 2 shows a schematic view of the sports training system of FIG. 1 in a training situation.

FIG. 2 shows a schematic view of the sports training system 1 of FIG. 1 in a training situation. The main training device 3 may be substantially the same as described above. The main training device 3 is preferably configured to be placed on the ground, for example on a sports field, but could also be mounted to a vertical wall. The at least one sensor 4a, 4b is preferably placed at an angle of more or less 5° with respect to the plane of placement, for example with respect to the ground, to avoid the measurements by the at least one sensor 4a, 4b to be too noisy due to for example weaving grass. The system 1 can include the central computing unit 8 and/or the mobile communication device 9 but need not. The main training device 3, or the system of separate devices, can also function independently without central computing unit 8 or mobile communication device 9. As soon as the system 1, for example the main training device 3 or the controller 5, the at least one stimulus generator 2a-2d and the at least one sensor 4a, 4b individually, has been activated, the user 10 can start training. The controller 5 may for example instruct the at least one stimulus generator 2a-2d to generate a first stimulus to the user 10. Such a stimulus can be the lightening up of for example a red LED light which may be indicative of a predetermined physical movement, for example move forward to a predetermined location on the sports field. This location may be flagged on the sports field using known cones or other types of beacons. The movement may also be a jump or moving a member of the body, for example lifting up a left arm, or any other physical movement to be trained. In a preferred embodiment of the invention, the controller 5 is configured to control the at least one stimulus generator 2a-2d based on the measurements by the at least one sensor 4a, 4b or based on data derived from the measurements by the at least one sensor 2. The at least one sensor 4a, 4b measuring a position of the user 10 during performance of the physical movement, the controller 5 can check whether or not the user 10 correctly performs the physical movement and can know when the user 10 has for example reached a predetermined position. Based on these measurements, the controller 5 can then be configured to have the at least one stimulus generator 2a-2d generate a next stimulus, for example only after having performed the triggered physical movement. In this way, the system 1 can follow a training pace of the user 10 instead of imposing the rhythm to the user 10. The controller 5 can even be configured to have the at least one stimulus generator 2a-2d generate a stimulus only when a user 10 has been detected by the at least one sensor 4a, 4b, for example within a predetermined range. As such, the user 10 can himself determine when to start a training. The controller 5 can be configured to comprise a set of predetermined training exercises, each including a sequence of stimuli to be generated by the at least one stimulus generator. A random sequence of stimuli can also be a possibility. Each stimulus may be associated with a predetermined physical movement, which may be different for each stimulus, or even for an aspect of the stimulus, for example red blinking light for moving forward and red continuous light for moving backwards, or for jumping forward instead of running etc. The user 10 can for example choose one of the training exercises and the controller 5 can control the at least one stimulus generator 2a-2d at a pace determined by the user 10 based on the measurements by the at least one sensor 4a, 4b. In a more advanced way, the controller 5 may also be configured to amend a predetermined sequence of a training exercise based on the measurements and data derived from said measurements by the at least one sensor 4a, 4b, for example when an analysis of the measurements and/or derived data shows a slower reaction time and/or speed and/or acceleration in a given direction. The controller 5 may also be configured to control the at least one stimulus generator or to amend a predetermined sequence of a training exercise based on further measurements on the user, such a heartbeat rate during performance of the physical movement. The sports training system 1 can further comprise one or more beacons 11 configured to indicate a predetermined distance from the at least one sensor 4a, 4b. Said beacons 11 are configured to visualize for the user 10 where the predetermined locations or checkpoints to be reached are on the sports field which are predetermined by the controller 5 and which may depend on the selection of the training exercise. The at least one beacon 11 is preferably detectable by the at least one sensor 4a, 4b so that correct placement of the beacons 11 can be checked. The beacons 11 may for example include a movable element which is detectable by for example a radar sensor. Alternatively, correct positioning of the beacons 11 may be detected by the at least one sensor 4a, 4b by measuring the position of the user 10 while positioning the beacons 11. The controller 5 may be configured to emit a signal when a beacon 11 has been correctly positioned with respect to a selected training exercise. Moreover, the at least one beacon 11 may include a stimulus generator which can be controlled by the controller 5, which may improve visibility of the stimulus generator, for example in relatively large sports fields. In a training situation as illustrated, a training system 1 as previously described has been provided and installed on the sports field. The user can select a training exercise including a sequence of stimuli to be generated and indicative for a predetermined physical movement. As a relatively simple example, an exercise may include running towards predetermined positions related to predetermined stimulus generators 2a-2d while always facing the main training device 3. A stimulus generated by stimulus generator 2a may for example correspond to a predefined distance or position from the main device 3 which may be visualized by positioning beacon 11a at said distance. Said beacon 11a may for example be of the same colour as the colour of the corresponding stimulus generator, which is illustrated by corresponding filling patterns between the stimulus generators 2a-2d and beacons 11a-11d. Once all beacons 11a-11d have been correctly positioned on the sports field, the controller 5 can control the at least one stimulus generator to generate a stimulus, for example have the stimulus generator 11a generate a first stimulus, which can optionally be done as soon as the at least one sensor 4a, 4b has detected the user 10. While the user 10 performs the triggered physical movement, for example is running towards beacon 11a, the at least one sensor 4a, 4b measures a position of the user 10 at predetermined time intervals, for example at a rate of thirty times per second. The beacons 11a-11d are only a visual aid to the user of the predetermined locations or checkpoints, but the training system may also work without said beacons and rely only on the virtual checkpoints. The controller 5 derives a trajectory of the user 10 during performance of the physical movement from the position measurements. In case of a radar sensor, the sensor can also measure a speed and/or a direction of movement of the user 10. As soon as the at least one sensor 4a, 4b detects the presence or passing of the user 10 at a predetermined position, the controller 5 can be configured to have the next stimulus generator, for example stimulus generator 2b generate a next stimulus, for example indicative of moving towards beacon 11b. In order to check the presence or passing of the user at the beacon, the controller 5 may include predetermined locations or checkpoints, which may comprise areas, for example of more or less 30 cm diameter, or linear checkpoints through which the user 10 needs to pass, which is detected by the at least one sensor 4a, 4b. It may for example be imposed to go round the beacon 11a, so there may be a linear checkpoint at a rear side of the beacon 11a which the user 10 has to cross, and which crossing is detectable by the at least one sensor 4a, 4b. The checkpoint is not a physical checkpoint, but a predetermined area known to the controller 5, for example defined by coordinates or in any other way known to the person skilled in the art. The checkpoint may also be a surface area rather than a linear checkpoint. The training exercise may for example include running to beacon 11a, then to 11b, then to 11c and then to 11d, each time going round the respective beacon and end when a presence of the user 10 has been detected at a checkpoint defined near beacon 11d. While beacons 11a and 11b may be well detectable by a first sensor 4a, the user 10 may in the first part of the exercise be moving substantially within a detection beam of said sensor 4a. While moving towards beacon 11c, the user 10 is moving towards a side of the detection beam of sensor 4a and then into the detection beam of sensor 4b, and while moving from beacon 11c to beacon 11d, the user 10 is moving into the side ranges of the detection beam of both sensors 4a and 4b. It is therefore desirable that the detection beams of the sensors at least partly overlap. Within this overlap, position measurements of both sensors can be combined, which combinations can compensate for a lower accuracy of measurement in a side region of a sensor detection beam. The measurement range and an angle of the detection beam of a sensor is preferably adjustable so that the measurement range and detection angle can be adjusted according to the needs of a training exercise. A smaller detection beam angle can generally allow a larger measurement range and vice versa. Combination of position measurements by a plurality of sensors can also increase accuracy to allow deriving more precise data on the physical movement of the user 10. In that way, movement of arms and legs, right and left, may for example be distinguishable. In case the training exercise includes a movement with an attribute, such as for example dribbling with a ball while moving and/or shooting a ball into a predefined direction, the controller 5 may also be configured to derive a trajectory of an object during performance of the physical movement from the position measurements of the user and of the object by the at least one sensor 4a, 4b. The controller 5, or more preferably the central computing unit 8, can store measured and derived data of a given training exercise performed by the user 10. The central computing unit 8 can then be configured to give detailed feedback to the user 10 on the performance of the triggered physical movements: not only on the reaction time and/or on the time needed to perform the entire exercise, but also on the trajectory, speed, acceleration, direction of movement, and other aspects at predetermined time intervals during the performance. This feedback may then be used to amend a training exercise, manually by the user 10, or in a more advanced embodiment, automatically by the controller 5 in a next performance of a similar exercise, or even during performance of the training exercise by for example including repetition of sequences which have been performed less well than a predetermined threshold, for example in reaction time, speed, or based on any other measured or derived data. The central computing unit 8 may also be configured to provide recommendations for training exercises based on previous performance of a user. In this way, the sports training system 1 can allow a relatively complete assessment of the performance of a user without hindering a user's performance by requiring a wearable such as a vest or even a mobile phone.

Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. In other words, it is contemplated to cover any and all modifications, variations or equivalents that fall within the scope of the basic underlying principles and whose essential attributes are claimed in this patent application. It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

The invention claimed is:

1. A sports training system for exercising reaction to stimuli, comprising:
   at least one stimulus generator being configured to generate a stimulus indicative for a physical movement to be performed by a user;
   at least one sensor configured to measure, without using a wearable item, a position of the user at predetermined time intervals during performance of the physical movement;
   a controller configured to control the at least one stimulus generator, wherein the controller is also configured to derive a trajectory of the user during performance of the physical movement from the position measurements by the at least one sensor;
   wherein the controller is configured to control the at least one stimulus generator based on the position measurements by the at least one sensor or based on data derived from the position measurements by the at least one sensor; at least one beacon configured to indicate a predetermined distance from the at least one sensor, wherein the at least one beacon is detectable by the at least one sensor.

2. The sports training system according to claim 1, wherein the at least one sensor comprises at least two sensors, each being configured to measure the position of the user within a respective detection beam at predetermined time intervals during performance of the physical movement.

3. The sports training system according to claim 2, wherein a first detection beam of one of the at least two sensors at least partly overlap with a second detection beam of another of the at least two sensors.

4. The sports training system according to claim 1, comprising a communication unit configured to transmit data related to the performance of the physical movement to a central computing unit for further analysis and/or storage of the data.

5. The sports training system according to claim 4, wherein the communication unit is configured to receive instructions for the at least one stimulus generator from the central computing unit and/or from a mobile communication device.

6. The sports training system according to claim 4, comprising a central computing unit configured to analyze the data received from the communication unit.

7. The sports training system according to claim 1, wherein the controller is configured to measure and/or derive a speed, a direction of movement and/or an acceleration of the user during performance of the physical movement from the measurements by the at least one sensor.

8. The sports training system according to claim 1, wherein the at least one beacon includes a stimulus generator which is controllable by the controller.

9. The sports training system according to claim 1, wherein the at least one sensor is configured to non-visually measure the position of the user during performance of the physical movement.

10. The sports training system according to claim 1, wherein a measurement range of the at least one sensor is adjustable.

11. The sports training system according to claim 1, wherein the controller is configured to derive a trajectory of an object during performance of the physical movement from the position measurements by the at least one sensor.

12. The sports training system according to claim 1, comprising an interface configured to display data derived by the controller related to the performance of the physical movement.

13. A sports training method for exercising reaction to stimuli comprising the steps of:
   providing the sports training system according to claim 1;
   controlling the stimulus generator to generate at least one stimulus;
   generating the stimulus indicative for the physical movement to be performed by the user;

measuring the position of the user at predetermined time intervals during performance of the physical movement;

deriving the trajectory of the user during performance of the physical movement from the position measurements.

\* \* \* \* \*